United States Patent
Zhang et al.

(10) Patent No.: US 9,567,636 B2
(45) Date of Patent: Feb. 14, 2017

(54) USE OF HLA-B*1301 ALLELE

(71) Applicant: Shandong Provincial Institute of Dermatology and Venereology, Jinan (CN)

(72) Inventors: Furen Zhang, Jinan (CN); Shumin Chen, Jinan (CN); Hong Liu, Jinan (CN)

(73) Assignee: Shandong Provincial Institute of Dermatology and V, Jinan, Shandong (CN)

( * ) Notice: Subject to any disclaimer, the term of this patent is extended or adjusted under 35 U.S.C. 154(b) by 0 days.

(21) Appl. No.: 14/370,465

(22) PCT Filed: Jun. 18, 2013

(86) PCT No.: PCT/CN2013/000714
§ 371 (c)(1),
(2) Date: Jul. 2, 2014

(87) PCT Pub. No.: WO2014/063433
PCT Pub. Date: May 1, 2014

(65) Prior Publication Data
US 2015/0218634 A1  Aug. 6, 2015

(30) Foreign Application Priority Data
Oct. 23, 2012 (CN) .......................... 2012 1 0407149

(51) Int. Cl.
C12Q 1/68 (2006.01)
C12P 19/34 (2006.01)
C07K 16/40 (2006.01)

(52) U.S. Cl.
CPC ....... *C12Q 1/6881* (2013.01); *C12Q 2600/106* (2013.01); *C12Q 2600/136* (2013.01); *C12Q 2600/156* (2013.01); *C12Q 2600/172* (2013.01)

(58) Field of Classification Search
CPC ............ C12Q 1/6881; C12Q 2600/106; C12Q 2600/156; C12Q 2600/172
See application file for complete search history.

(56) References Cited

U.S. PATENT DOCUMENTS

2005/0100926 A1* 5/2005 Chen ................... C12Q 1/6881
435/6.13
2006/0183146 A1 8/2006 Athanasiou et al.

FOREIGN PATENT DOCUMENTS

CN  102925567 A  2/2013

OTHER PUBLICATIONS

Shi Y.-W. et al . Basic & Clinical Pharmacology & Toxicology, 2012, 111, 58-64.*
'Dapsone Side Effects Center' from rxlist.com, printed on Nov. 18, 2015, pp. 1-5.*
Madhi B.M. et al. Mahdi Clinical and Translational Medicine 2013, 2:6, pp. 1-5.*
Pal P. et al. The Prostate 69:1548-1556 (2009).*
Wall J.D. et al. Nature Reviews—Genetics (2003) vol. 4, pp. 587-597.*
Thisted R.A. What is a P-value? http://www.stat.uchicago.edu/~thisted (1998) pp. 1-6.*
Wang H. et al. Journal of Investigative Dermatology (2013) 133, pp. 2642-2644 and Supplementary Information and Tables.*
Roujeau J.-C. Allergology International. 2006;55:27-33.*
Qin, Junjian et al., The association between polymorphism of HLA-B allele and immunoglobulin—a nephropathy in southern Chinese Han population, Chinese Journal Clinicians, Dec. 2011, vol. 5, No. 24, pp. 7191-7195.

* cited by examiner

*Primary Examiner* — Stephen Kapushoc
(74) *Attorney, Agent, or Firm* — Knobbe Martens Olson and Bear, LLP

(57) ABSTRACT

The present invention discloses uses of a HLA-B*1301 allele, comprising: 1) a use of a substance for detecting whether a person has the HLA-B*1301 allele in preparation of a product for evaluating a risk of adverse drug reactions in response to dapsone in the person; 2) a method for detecting or evaluating a risk of adverse drug reaction in response to dapsone in a person, comprising detecting whether the person has the HLA-B*1301 allele, wherein, a person with LA-B*1301 allele suffers a higher risk of adverse drug reaction upon being administered dapsone, as compared with a person without HLA-B*1301 allele, and a person with LA-B*1301 alleles at both chromosomes of a pair of homologous chromosomes suffers a higher risk of adverse drug reaction upon being administered dapsone, as compared with a person with HLA-B*1301 allele at only one of a pair of homologous chromosomes.

3 Claims, 2 Drawing Sheets

SEQUENCE LISTING

```
<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<223> OTHER INFORMATION: oligonucleotide
<220> FEATURE:
<221> NAME/KEY: misc_feature
<222> LOCATION: (3)..(3)
<223> OTHER INFORMATION: s=g or c

<400> SEQUENCE: 1
ggsagggaaa tggcctct                                                 18

<210> SEQ ID NO 2
<211> LENGTH: 19
<212> TYPE: DNA
<213> ORGANISM: Artificial sequence
<220> FEATURE:
<223> OTHER INFORMATION: oligonucleotide

<400> SEQUENCE: 2
ggatggggag tcgtgacct                                                19

<210> SEQ ID NO 3
<211> LENGTH: 19
<212> TYPE: DNA
<213> ORGANISM: Artificial sequence
<220> FEATURE:
<223> OTHER INFORMATION: oligonucleotide

<400> SEQUENCE: 3
gcgtttaccc ggtttcatt                                                19

<210> SEQ ID NO 4
<211> LENGTH: 20
<212> TYPE: DNA
<213> ORGANISM: Artificial sequence
<220> FEATURE:
<223> OTHER INFORMATION: oligonucleotide

<400> SEQUENCE: 4
cggcgaccta taggagatgg                                               20
```

USE OF HLA-B*1301 ALLELE

TECHNICAL FIELD

The present invention relates to uses of the HLA-B*1301 allele, in particular, a use of the HLA-B*1301 allele as a genetic marker of the risk of dapsone syndrome.

REFERENCE TO SEQUENCE LISTING

A Sequence Listing submitted as an ASCII text file via EFS-Web is hereby incorporated by reference in accordance with 35 U.S.C. §1.52(e). The name of the ASCII text file for the Sequence Listing is 2014-07-02 Sequence Listing—JEEK17.001APC.TXT, the date of creation of the ASCII text file is Jul. 2, 2014, and the size of the ASCII text file is 1.13 KB.

TECHNICAL BACKGROUND

MHC (major histocompatibility complex) is a gene complex related to graft rejection. A human MHC is referred to as HLA (Human Leukocyte A system). Rich polymorphism is an essential feature of the HLA gene system. There are a variety of variants, in human populations, of the DNA sequences in many gene loci in the HLA complex, which variants are called alleles. The HLA allele system is located at the sixth chromosome. Since human is a randomly mating heterozygous population, the probability that two HLA alleles are completely the same is little for each individual, not only making HLA be a system with most abundant polymorphism in human body, but also making the HLA allele and a product thereof in each individual be a biological "identity card" for the uniqueness possessed by this individual, i.e., a marker of an individuality. The polymorphism of the HLA system ensures suitable immune responses of the population to various pathogens such that the continuation of the population is guaranteed and the stability thereof is maintained. Many HLA molecules have been found to be associated with drug reactions in different populations. For example, the HLA-B*1502 alleles in Chinese population and Thai population, or the HLA-A*3101 alleles in Caucasian population and Japanese population are related to drug hypersensitivity reactions resulted from Carbamazepine; the HLA-B*5701 alleles in Caucasian population are related to drug reactions resulted from Abacavir; the HLA-B*5801 alleles in Chinese population are related to drug reactions resulted from Allopurinol. No drug reaction is found to be attributed to the HLA-B*1301 allele up to now, however, it is previously reported that this locus was related to allergic dermatitis resulted from trichloroethylene (an industrial solvent) (Li H, Dai Y, Huang H, et al. HLA-B*1301 as a biomarker for genetic susceptibility to hypersensitivity dermatitis induced by trichloroethylene among workers in China. Environ Health Perspect 2007; 115:1553-6).

Dapsone (4,4'-diamino diphenyl sulfone, DDS), synthesized in 1908, is anti-infective and anti-inflammatory. This drug, alone or in combination with other drugs, may be widely used in the treatment of infectious diseases (such as leprosy, malaria, diseases induced by *Actinomyces* infection, and *pneumocystis carinii* pneumonia due to HIV infection), or in the treatment of chronic inflammatory diseases characterized in abnormal infiltration of neutrophils or eosinophils (such as autoimmune bullous disease, persistent uplift erythema, pustular psoriasis, pyoderma gangrenosum, acne). In addition, this drug may further serve to treat rheumatic arthritis, and at the same time protect, in a certain degree, the nerves of the patient with acute ischemic stroke.

Previous epidemiological studies showed that about 0.5-3% of the patients receiving DDS treatment may suffer from drug hypersensitivity syndrome, with a mortality rate of about 11-13%. As early as 1949, Lowe noticed this phenomenon; and this disease was formally designated as "dapsone hypersensitivity syndrome" (DHS) in 1951. DHS, a serious heterogeneous reaction of an individual to a drug, often occurs within 4-6 weeks after the DDS treatment, with the clinical manifestations including high fever, rash, and visceral involvement (typically liver and blood system involvement), and even organ failure in severe condition. With DDS employed worldwide in combined chemotherapy of leprosy and chemoprevention of *pneumocystis carinii* pneumonia due to HIV infection, the incidence of DHS is increased dramatically. A recent systematic review for a published epidemiological article summarizes that the prevalence rate of DHS is about 1.4%. However, there is no reliable detection method available for predicting the risk of DHS by now.

SUMMARY OF THE INVENTION

The technical problem to be solved by the present invention is to provide a novel use of the HLA-B*1301 allele as a genetic marker of the risk of dapsone syndrome.

The novel use as provided by the present invention is at least one of the following:
1) use of a substance, for detecting whether a person has the HLA-B*1301 allele, in preparation of a product for detecting or evaluating the risk of adverse drug reactions in response to dapsone in the person;
2) use of a substance, for detecting whether a person has the HLA-B*1301 allele, in preparation of a product for detecting or evaluating the risk of dapsone hypersensitivity syndrome in the person;
3) use of a substance, for detecting whether a person has the HLA-B*1301 allele, in preparation of a product for screening a dapsone hypersensitivity syndrome;
4) a method for detecting or evaluating a risk of adverse drug reaction in response to dapsone in a person, comprising detecting whether the person has the HLA-B*1301 allele, wherein, a person with HLA-B*1301 allele suffers a higher risk of adverse drug reaction upon using dapsone, as compared with a person without HLA-B*1301 allele, and a person with HLA-B*1301 alleles at both chromosomes of a pair of homologous chromosomes suffers a higher risk of adverse drug reaction upon using dapsone, as compared with a person with HLA-B*1301 allele at only one of a pair of homologous chromosomes;
5) a method for detecting or evaluating a risk of developing dapsone hypersensitivity syndrome in a person, comprising detecting whether the person has the HLA-B*1301 allele, wherein, a person with HLA-B*1301 allele suffers a higher risk of dapsone hypersensitivity syndrome upon using dapsone, as compared with a person without HLA-B*1301 allele, and a person with HLA-B*1301 alleles at both chromosomes of a pair of homologous chromosomes suffers a higher risk of dapsone hypersensitivity syndrome upon using dapsone, as compared with a person with HLA-B*1301 allele at only one of a pair of homologous chromosomes;
6) a method developed for treating adverse drug reactions in response to dapsone, comprising identifying and/or screening a candidate drug with a detection method using the HLA-B*1301 allele as a target;

7) a method developed for treating dapsone hypersensitivity syndrome, comprising identifying and/or screening a candidate drug with a detection method using the HLA-B*1301 allele as a target;

8) a product for detecting or evaluating a risk of developing adverse drug reaction in response to dapsone in a person, comprising a substance for detecting whether a person has the HLA-B*1301 allele.

Wherein, the substance for detecting whether a person has the HLA-B*1301 allele in the above 1), 2), 3) and 8) may be a reagent, a kit and/or a device used in any of the methods for detecting the presence of an allele as known in the art. For example, the reagent, the kit and/or the device used for determining the presence of the HLA-B*1301 allele by at least one of the following methods: DNA specific hybridization, PCR-based HLA sequence typing as well as HLA serotyping. Wherein, the PCR primers employed in the PCR-based HLA sequence typing may be primer pair 1 and/or primer pair 2, in particular. Said primer pair 1 consists of the single-stranded DNA as set forth in SEQ ID No.1 and SEQ ID No.2; and the primer pair 2 consists of the single-stranded DNA as set forth in SEQ ID No.3 and SEQ ID No.4. In one Example of the present invention, the substance for detecting whether a person has the HLA-B*1301 allele in the above 1), 2), 3) and 8) is the primer pair 1 and/or primer pair 2, or a kit comprising said primer pair 1 and/or primer pair 2.

The substance for detecting whether a person has the HLA-B*1301 allele in the above 1), 2), 3) and 8) may further be a reagent, a kit and/or a device used in a method for detecting whether a person has an equivalent genetic marker of the HLA-B*1301 allele, whose presence indicates the presence of the HLA-B*1301 allele. The detection of whether a person has the HLA-B*1301 allele in the above 4) and 5) may further be determined by detecting an equivalent genetic marker of the HLA-B*1301 allele, whose presence indicates the presence of the HLA-B*1301 allele. The equivalent genetic marker is a genetic marker connected to the HLA-B*1301 allele. The equivalent genetic marker may be a single nucleotide polymorphism (abbreviated to SNP), a simple sequence repeat (SSR) marker, and the like, such as rs114740545, rs116111301, rs115901473, rs115087954, rs115675600, rs187280524, rs114242707, rs117901686, rs144295468, rs116670002, rs114025781, rs150578601, rs184663538, rs147436789, rs116727474, rs181134814, rs114738037, rs116559955, rs140019442, rs115099160, rs114269118, rs116702376, rs114044189, rs75031011, rs114703573, rs116990865, rs116352528, rs115467821, rs114557543, rs115169469, rs114174160, rs148933000, rs139232749, rs191781678, rs116299045, rs115919658, rs184804684, rs115314010, rs114560740, rs116664449, rs116590236, rs114042808, rs115282162, rs191351745, rs142449668, rs138476012, rs116791918, rs114619879, rs145574701, rs186013251, rs116394756, rs144957773, rs149868923, rs117015327, rs146938564, rs144519211, rs116800609, rs115438047, rs116238756, rs115579895, rs114934557, rs115644116, rs184278614, rs115512397, rs117674267, rs117357765, rs187285424, rs115938217, rs144112558, rs143310386, rs117948233, rs116143597, rs115618393, rs118069711, rs114558979, rs114430391, rs116545227, rs114871120, rs186776456, rs115144194, rs114466888, rs116050364, rs117554535, rs138890419, rs117416412, rs187053286, rs138585202, rs114790460, rs182307981, rs116799594, rs117177835, rs115493428, rs147420529, rs143510919, rs115271465, rs148814200, rs146667604, rs145848766, rs116182888, rs139753005, rs151055597, rs142876154, rs114596560, rs147187739, rs117882759, rs150312141, rs138525703, rs150009117, rs114955269, rs141690290, rs114673459, rs115461077, rs190715652, rs116270078, rs189405064, rs115840422, rs141629269, rs145194724, rs149956121, rs139220743, rs193127702, rs116309554, rs114342076, rs139930000, rs145959074, rs142459425, rs182634314, rs137882198, rs115709299, rs149636715, rs150064319, rs190220726, rs114486436, rs139261704, rs142035154, rs146509511, rs188267792, rs183291469, rs114495987, rs116690463, rs142716612, rs115326349, rs114215172, rs115305111, rs150528380, rs114842164, rs115766057, rs116766359, rs114463114, rs150105195, rs142447081, rs114212906, rs114475434, rs115827739, rs189111115, rs115681000, rs116255593, rs115130140, rs116619302, rs115660274, rs115068492, rs115683494, rs116193620, rs114233831, rs115655546, rs116812555, rs115586038, rs115967895, rs115837294, rs185848342, rs117652729, rs192118756, rs189253569, rs116429420, rs115212249, rs116599568, rs115588141, rs117168997, rs116208261, rs115372244, rs118005849, rs117246836, rs117200577, rs114618162, rs111841098, rs114370548, rs115788187, rs137884196, rs114251983, rs115690605, rs116815392, rs114999980, rs116234368, rs117604452, rs115646358.

In practice, the second-generation sequencers such as the Genome Sequencer FLX system developed by Roche 454 Life Sciences and PCR-SSOP-Luminex (the main devices are Luminex100, 200, 3D flow Luminexs from US Luminex Corporation), PCR-SSP, Sanger Sequencing (the first-generation sequencers from the ABI company, 3130, 3130XL, 3730, 3730XL) and the like may be used to detect whether a person has the HLA-B*1301 allele.

The product in the above 1), 2), 3) and 8) may be a reagent or a kit, or even a combined product of a reagent or a kit with a device.

The detection of whether a person has the HLA-B*1301 allele in the above 4) and 5) may adopt any of the methods for detecting the presence of an allele known in the art, such as DNA specific hybridization, PCR-based HLA sequence typing and/or HLA serotyping.

In the above uses, DNA, RNA, proteins, cells or sera prepared from the peripheral blood of a person to be detected may be used to detect whether the person has the HLA-B*1301 allele.

In the above 6) and 7), particularly, an isolated cell expressing the HLA-B*1301 allele may be contacted with the drug to be tested, and then, the drug bound to the HLA-B*1301 allele, prone to inhibiting expression and/or function of the HLA-B*1301 allele, is used as a candidate drug to further test the efficacy thereof for treating adverse drug reactions in response to dapsone, such as dapsone hypersensitivity syndrome.

Said adverse drug reaction is an undesired and non-intended drug effect, such as the adverse reactions arise at a dose for preventing, diagnosing or treating a disease. If a patient has a higher probability of developing adverse drug reactions than that of general population, this patient is at a risk of developing adverse drug reactions.

In one Example of the present application, the results of a study conducted on a population consisted of 76 DHS patients and 1034 non-DHS clinical controls indicate that a person with one HLA-B*1301 allele (only one of a pair of homologous chromosomes carries the HLA-B*1301 allele), after being administered DDS, is at a risk of DHS 37.53 times of that of a person without HLA-B*1301 allele (confidence level, 0.95; confidence interval, (18.80, 74.94)); a person with two HLA-B*1301 risk alleles (a pair of homologous chromosomes both carry the HLA-B*1301 allele), after being given DDS, is at a risk of DHS 110.8 times of that of a person without HLA-B*1301 allele (confidence level, 0.95; confidence interval, (25.85, 474.54)).

A shows that HLA-B*1301 (indicated by a arrow) is the most significantly correlated allele in the MHC region. The recombination rate is expressed with the light blue peak figure. The SNPs, alleles and amino acids as imported are indicated with circles, and the sorted SNPs are indicated with rhombuses. Different colors represent the degree of correlation of these SNPs, alleles and amino acids with the HLA-B*1301 locus. Red, correlation coefficient >0.8; orange, correlation coefficient=0.5-0.8; yellow, correlation coefficient=0.2-0.5; gray, correlation coefficient <0.2; and white, correlation coefficient=0.

B shows the correlated signal chart in the MHC region after condition analysis by controlling the HLA-B*1301 locus; no remaining correlated signal is observed, demonstrating that only one individual signal, HLA-B*1301, is present in this region.

Figure 2:
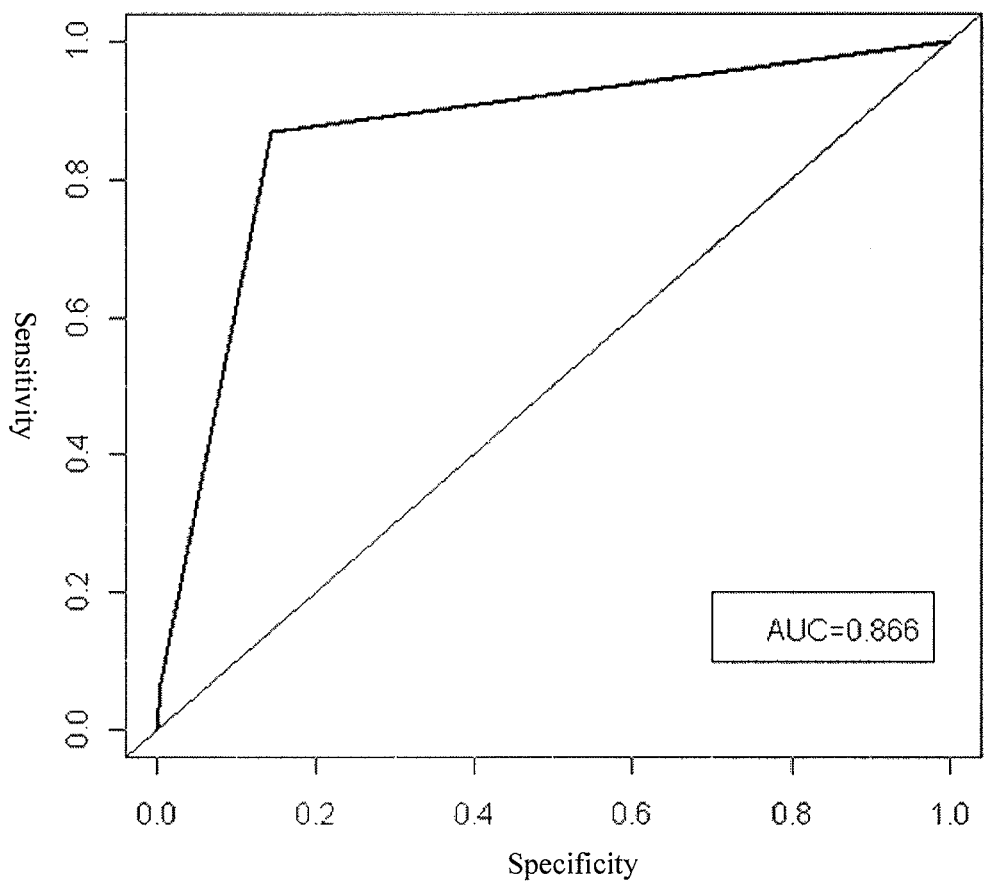

FIG. 2 is the receiver operating characteristic curve for the risk prediction conducted on DHS using HLA-B*1301 as a predictive marker.

BEST MODE FOR CARRYING OUT THE INVENTION

The following Examples, which are not intended to limit the present invention, are provided so that the present invention can be better understood. All the experimental methods used in the following Examples are conventional methods unless specifically indicated.

All materials, reagents and the like used in the following Examples are commercially available unless specifically indicated.

Example 1

The HLA-B*1301 allele is a genetic marker of the risk of dapsone hypersensitivity syndrome.
I. Samples The samples were peripheral blood taken from human, including case samples, clinical control samples and healthy control samples.
1. Case Samples 76 Chinese DHS patients (39 for the discovery-phase study, and 37 for the validation-phase study) were included in the study. These 76 patients were administered DDS when receiving combined chemotherapy against leprosy. The male-to-female ratio in the patients, aged 38 years old in average, was 1.6:1. From the initial administration of DDS to the occurrence of DHS clinical symptoms, it took 2-8 weeks (32.79 days in average). The most common skin lesion was maculopapule (57.7%), secondly exfoliative dermatitis (38.5%), scarlatiniform erythema (7.7%), and oral erosion (1.3%). The system involvement symptoms included: fever (83.1%), abnormal liver function (74.4%), and swollen lymph glands (34.6%). The laboratory examination results showed abnormal increase level of liver enzymes in serum: 58 patients were shown significantly increased in the level of alanine transaminase, 49 patients significantly increased in the level of aspartate aminotransferase, 37 patients decreased in the level of hemoglobin, and 35 patients abnormally increased in the level of serum bilirubin. The diagnosis of DHS was based on the medical history, clinical manifestations and laboratory examinations of the patients.
2. Clinical Control Samples The clinical control samples of the study included 1034 non-DHS patients (833 for the discovery phase, and 201 for the validation phase). Each of these 1034 non-DHS patients had been be attacked by leprosy, and received DDS as a part of the combined chemotherapy regime for the treatment of leprosy, and the clinical symptom or abnormal biological indicator of DHS was observed in none of these clinical control samples.

These clinical control samples and case samples were matched geographically and ethnically on the whole.
3. Healthy Control Samples The healthy control samples in the study included 1944 healthy controls for evaluating the frequency of HLA-B*1301 in Chinese population, wherein 951 samples were from Guangdong, 523 from Shandong, and 470 from Yunnan.

Where diagnosis for a patient with leprosy was established based on two or more, or the third rule of the following four diagnostic criteria: 1. skin lesions associated with sensory disturbance and ischidrosis, or with a numbness area; 2. peripheral nerve involvement, represented as thick neural stem associated with corresponding dysfunction; 3. *Mycobacterium leprae* was detected in the tissue sections or tissue fluid smears of the skin lesions; 4. pathologically visible changes in characteristic.

The diagnostic criteria for healthy controls: no medical history of leprosy and other infectious diseases, and no medical history and family history of other autoimmune diseases.
II. Methods
1. The Discovery Phase Genotyping was performed on 39 DHS patients in the case samples and 833 non-DHS patients in the clinical control samples using Illumina-660 chip (Illumina Human 660W-Quad beadchip). A total of 430,276 SNPs from the 39 DHS patients and 833 non-DHS patients were used in data analysis in the discovery phase of Genome-Wide Scan.

Figure 1:
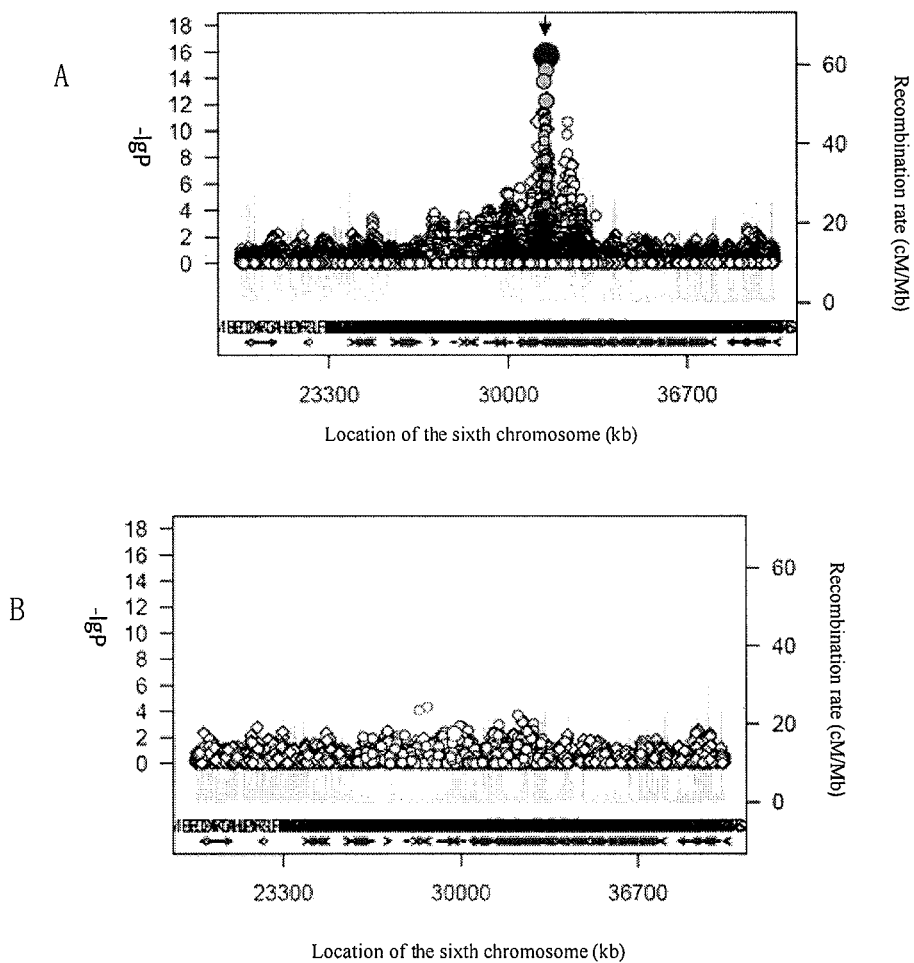
FIG. 1 shows correlated signals of the HLA region.

Import analysis of the HLA allele (dichotomy and quartile) and amino acids was conducted, using the Asian HAPMAP (the international HapMap project) reference sequences (totally 178 individuals including Han Chinese from Beijing, Chinese from Tokyo, and Japanese), on each individual of the 39 DHS patients in the case samples and 833 non-DHS patients in the clinical control samples, a total of 66 typical HLA dichotomy alleles, 118 typical quartile HLA alleles, 497 polymorphic amino acid positions and 4206 SNPs were imported, which were subjected to correlation analysis together with 4636 SNPs resulted from sorting. As shown by the results of the correlation analysis (A in FIG. 1), the single nucleotide polymorphism site located in the MHC region of the sixth chromosome (a physical distance of 26,000,000-34,000,000) (NCBI build 37) was correlated with the dapsone hypersensitivity syndrome resulted upon clinical use of dapsone.

A logistic regression analysis was performed on this region to define the positively correlated signal at HLA-B*1301 and HLA-C*0304 loci. The correlation coefficient between these two loci was 0.74. In addition, the correlation analysis conducted on the HLA-B*13 dichotomy alleles and 497 polymorphic amino acid positions showed that although there were correlated signals between them, the signals each was weaker than that of HLA-B*1301. No other independent signal was observed in the MHC region when the HLA-B*1301 was controlled (B in FIG. 1). In a word, it was demonstrated that HLA-B*1301 was the mian allele of the DHS risk, HLA-B*1301 (P=2.04×10$^{-16}$; OR was 21.67, confidence level, 0.95, confidence interval (10.41, 45.12)).

2. The Validation Phase

To further verify the correlation of HLA-B*1301 allele, the 454 sequencing platform (Genome Sequencer FLX system developed by Roche 454 Life Sciences) was employed to conduct HLA sorting on another 37 DHS patients in the case samples and another 201 non-DHS patients in the clinical control samples (randomizedly selected from a total of 1089 validation controls). Wherein, PCR amplification was conducted on genomic DNA isolated from the peripheral blood of the samples for the HLA-B*1301 allele using primer pair 1 and primer pair 2, respectively. The primer pair 1 consists of the single-stranded DNA as set forth in SEQ ID No.1 and SEQ ID No.2; and the primer pair 2 consists of the single-stranded DNA as set forth in SEQ ID No.3 and SEQ ID No.4.

Recall of the HLA allele was performed at GATK using HLA Caller software, the sudsequent correlation analysis was conducted with the logistic regression method, and the results showed HLA-B*1301 (OR=23.54, confidence level, 0.95, confidence interval (8.71, 63.62); P=4.74×10$^{-10}$).

3. Combination Analysis

The HLA-B*1301 allele was found to be strongly correlated with DHS: (OR=22.32, confidence level, 0.95, confidence interval, (12.40, 40.28); P=6.32×10$^{-25}$) after analyzing data from the discovery and validation phases in combination.

The 454 sequencing platform (Genome Sequencer FLX system developed by Roche 454 Life Sciences) was employed to conduct HLA sorting on 76 DHS patients in the case samples and 1034 non-DHS patients in the clinical control samples, and the sorting results are shown in Table 1.

TABLE 1 the HLA sorting results

| Samples | Non-HLA-B*1301 carriers | HLA-B*1301 heterozygous carriers | HLA-B*1301 homozygous carriers |
|---|---|---|---|
| DHS patients (N = 76) | 10 (13.2%) | 61 (80.3%) | 5 (6.6%) |
| controls (N = 1034) | 886 (85.5%) | 144(13.9%) | 4 (0.4%) |

Note:
N in the first column denotes the number or total samples; in columns 2-3, the numerical values outside the brackets denote the number of samples, the percentages inside the brackets denote the ratios of the numerical values outside the brackets to the number of total samples.

As can be seen from the results of table 1, among the 76 DHS patients, the number of true positive samples (HLA-B*1301 carriers) was 66, the number of false negative samples (non-HLA-B*1301 carriers) was 10; among the 1034 non-DHS patients, the number of true negative samples (non-HLA-B*1301 carriers) was 886, the number of false positive samples (HLA-B*1301 carriers) was 148. The risk prediction conducted on DHS, using HLA-B*1301 as the predictive marker, had a sensitivity of 86.84%, and a specificity of 85.69% (FIG. 2), wherein, sensitivity=the number of true positive samples/(the number of true positive samples+the number of false negative samples)×100, specificity=the number of true negative samples/(the number of true negative samples+the number of false positive samples)×100. The HLA-B*1301 heterozygous carriers were at a risk of DHS of $OR_{het}$=61×886/10×144=37.53 (confidence level, 0.95; confidence interval (18.80, 74.94)); the HLA-B*1301 homozygous carriers were at a risk of DHS of $OR_{hom}$=5×886/10×4=110.75 (confidence level, 0.95; confidence interval (25.85, 474.54)). As can be seen, the HLA-B*1301 allele was carried by 86.8% (66/76) of the DHS patients, and only by 14.3% (148/1034) of the non-DHS patients. As shown by the result, where an individual carried one HLA-B*1301 risk allele (HLA-B*1301 heterozygous carrier), this individual was at a risk of DHS, after being administered DDS, 37.53 times of that of an individual without the HLA-B*1301 allele (confidence level, 0.95; confidence interval (18.8, 74.9)); and where an individual carried two HLA-B*1301 risk alleles (HLA-B*1301 homozygous carrier), this individual was at a risk of DHS, after being administered DDS, 110.8 times of that of an individual without the HLA-B*1301 allele (confidence level, 0.95; confidence interval (25.9, 474.5)).

A recent review regarding the Asian population deduced that the prevalence rate of DHS was 1.4% (Lorenz, Wozel et al. 2012). Based on this prevalence rate, the positive predictive value was 7.9%, the negative predictive value was 99.8%, the positive likelihood ratio was 6.07, and the negative likelihood ratio was 0.1536, upon calculation. According to the positive likelihood ratio of 6.07, the risk of DHS in individuals with the HLA-B*1301 will be raised to 7.9%; and according to the negative likelihood ratio of 0.1536, the incidence of DHS in individuals with the HLA-B*1301 will be decreased from 1.4% to 0.2%. A screening for the HLA-B*1301 allele performed on patients in need of DDS treatment showed that the incidence of DHS in positive carriers may be greatly decreased from 1.4% to 0.2% without administering the drug.

According to the data resulted from 1944 healthy controls from the healthy control samples (from provinces, Shandong, Guangdong and Yunnan), the HLA-B*1301 allele had a frequency of 3.3% in Shandong samples, a frequency of 7.1% in Yunnan samples, and a frequency of 8.2% in Guangdong samples, which was consistent with the report in the allele database that the HLA-B*1301 allele had a frequency of (2-5%) in north Chinese population, and a frequency of (5-20%) in southern Chinese population. In the light of the relative prevalence of this locus in Chinese population as well as in some Asian countries, HLA-B*1301 screening and risk evaluation before administration of DDS will be of great benefit.

INDUSTRIAL APPLICATION

In practice, the presence or absence of HLA-B*1301 allele may be detected to predict whether a patient in need of DDS treatment will be attacked with DHS. A risk prediction may be made based on the detection result. Individuals with HLA-B*1301 are suggested to be treated with other drugs instead of the DDS treatment which may lead to drug hypersensitivity reaction. Individuals without HLA-B*1301 are safe to use DDS since DDS treatment would lead to drug hypersensitivity reaction at a very low probability.

What is claimed is:

1. A method for treating a condition selected from the group consisting of an infectious disease, a chronic inflammatory disease characterized by abnormal infiltration of neutrophils or eosinophils, rheumatic arthritis and acute ischemic stroke in a subject in need thereof, said method comprising:
   (a) obtaining a sample from the subject, said sample comprising nucleic acids, which comprise a polynucleotide encoding an HLA-B allele;
   (b) detecting the absence of a HLA-B*1301 allele in the polynucleotide encoding the HLA-B allele in the sample from the subject by analyzing the nucleic acids in the sample; and
   (c) administering dapsone to the subject, thereby treating the condition in the subject, wherein the subject has a reduced risk of developing dapsone hypersensitivity syndrome (DHS) in response to the administering of the dapsone as compared to a subject with at least one allele of HLA-B*1301.

2. The method according to claim 1, wherein said analyzing the nucleic acids in the sample comprises a method selected from the group consisting of DNA specific hybridization, and PCR-based HLA sequence typing.

3. The method according to claim 2, wherein analyzing the nucleic acids in the sample comprises PCR-based HLA sequence typing.

* * * * *